(12) United States Patent
Hoffman et al.

(10) Patent No.: US 7,955,241 B2
(45) Date of Patent: *Jun. 7, 2011

(54) MULTI-MODE PELVIC EXERCISE PROBE

(75) Inventors: Craig A. Hoffman, Waco, TX (US); Gerry M. Hoffman, Fort Worth, TX (US); Michael J. England, Forth Worth, TX (US)

(73) Assignee: Anatasol, LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/633,567

(22) Filed: Dec. 8, 2009

(65) Prior Publication Data

US 2010/0087757 A1    Apr. 8, 2010

Related U.S. Application Data

(63) Continuation of application No. 11/621,796, filed on Jan. 10, 2007, now Pat. No. 7,628,744, which is a continuation-in-part of application No. 11/268,923, filed on Nov. 8, 2005, now Pat. No. 7,645,220.

(51) Int. Cl.
*A63B 71/00* (2006.01)
(52) U.S. Cl. .......................................... 482/148; 600/29
(58) Field of Classification Search .......... 482/111–113, 482/148; 600/29, 46, 410, 591, 45, 30, 38; 607/138; 128/903–905; 73/379.01, 379.08
See application file for complete search history.

(56) References Cited

U.S. PATENT DOCUMENTS

| | | |
|---|---|---|
| 1,928,893 A | 10/1933 | Hoard |
| 2,507,859 A | 5/1950 | Kegel |
| 2,763,265 A | 9/1956 | Waters |
| 3,626,931 A | 12/1971 | Bysakh |
| 3,669,100 A | 6/1972 | Csanad |
| 3,933,147 A | 1/1976 | Du Vall et al. |
| 4,007,735 A | 2/1977 | Magnusson |
| 4,048,985 A | 9/1977 | Sasse |
| 4,216,783 A | 8/1980 | Kaiser et al. |
| 4,396,019 A | 8/1983 | Perry, Jr. |
| 4,653,514 A | 3/1987 | Shapiro |
| 4,911,149 A | 3/1990 | Borodulin et al. |
| 5,184,619 A | 2/1993 | Austin |
| 5,233,987 A | 8/1993 | Fabian et al. |
| 5,483,832 A | 1/1996 | Pauser et al. |
| 5,554,092 A | 9/1996 | Harpstead et al. |
| 5,662,699 A | 9/1997 | Hamedi et al. |
| 5,674,238 A | 10/1997 | Sample et al. |
| 5,733,230 A | 3/1998 | Sawchuck et al. |

(Continued)

*Primary Examiner* — Lori Baker
(74) *Attorney, Agent, or Firm* — Scott T. Griggs; Griggs Bergin LLP

(57) ABSTRACT

A perineometer exercise probe for home or clinical use assesses the strength of pelvic floor muscles and provides audible, visual and tactile biofeedback signals as training aids during pelvic exercises. The exercise probe is selectively operable in a passive reaction mode, in which audible, visual and tactile biofeedback signals proportional to pelvic muscle contractions are generated, and in an active vibrating mode in which therapeutic vibrations are applied directly to internal pelvic musculature with or without co-generation of biofeedback signals proportional to the strength of pelvic muscle contractions; and in a combination of both modes simultaneously. The probe reacts the pelvic contraction forces and thus provides passive tactile feedback signals that are experienced simultaneously with audible, visual and vibration-induced tactile biofeedback signals for improving the endurance and strength of pelvic floor muscles. Biofeedback signaling is facilitated by wireless two-way communication between the probe and a portable monitor.

20 Claims, 12 Drawing Sheets

U.S. PATENT DOCUMENTS

| | | |
|---|---|---|
| 5,782,745 A | 7/1998 | Benderev |
| 5,800,501 A | 9/1998 | Sherlock |
| 5,924,984 A | 7/1999 | Rao |
| 6,030,338 A | 2/2000 | Benderev |
| 6,063,045 A | 5/2000 | Wax et al. |
| 6,169,914 B1 | 1/2001 | Hovland et al. |
| 6,183,428 B1 | 2/2001 | Kilgore |
| 6,217,529 B1 | 4/2001 | Wax et al. |
| 6,625,495 B1 | 9/2003 | Alon et al. |
| 6,672,996 B2 | 1/2004 | Ross et al. |
| 6,741,895 B1 | 5/2004 | Gafni et al. |
| 6,807,444 B2 | 10/2004 | Tu et al. |
| 6,905,471 B2 | 6/2005 | Leivseth et al. |
| 6,964,643 B2 | 11/2005 | Hovland et al. |
| 7,628,744 B2 * | 12/2009 | Hoffman et al. .............. 482/148 |
| 7,645,220 B2 * | 1/2010 | Hoffman et al. .............. 482/148 |
| 2002/0055422 A1 | 5/2002 | Airmet et al. |
| 2003/0158475 A1 | 8/2003 | Johnson et al. |
| 2005/0090819 A1 | 4/2005 | Goble |
| 2007/0010702 A1 | 1/2007 | Wang et al. |
| 2007/0135717 A1 | 6/2007 | Uenishi et al. |
| 2009/0007672 A1 | 1/2009 | Pletner et al. |

\* cited by examiner

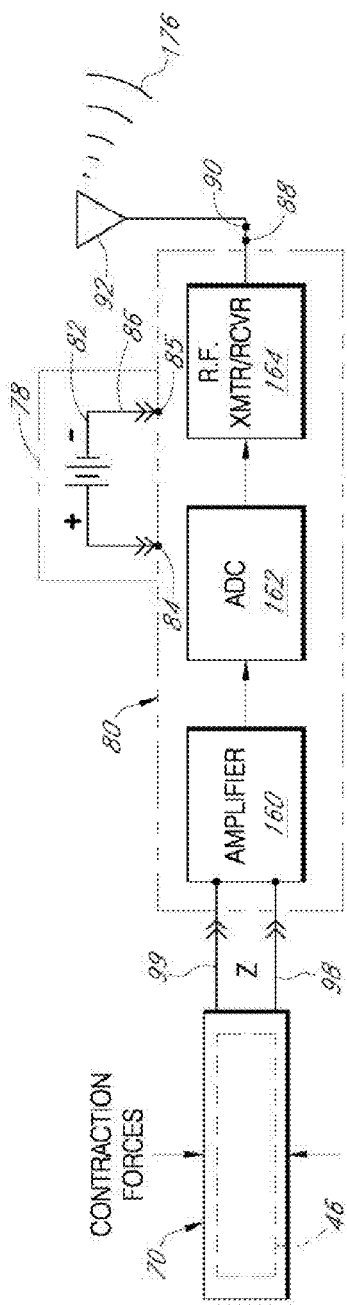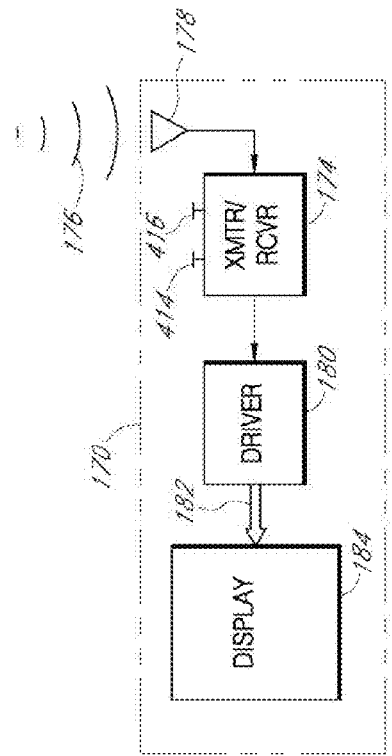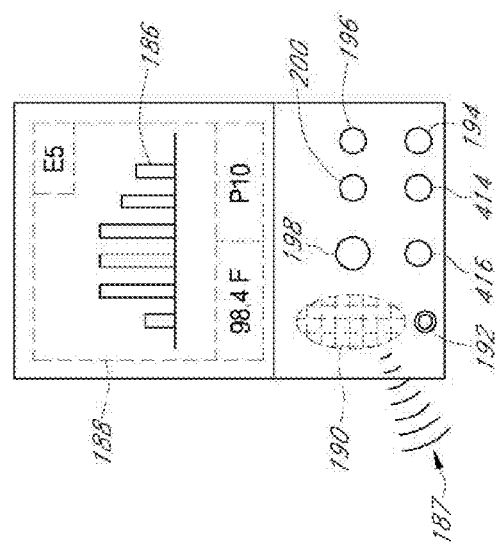

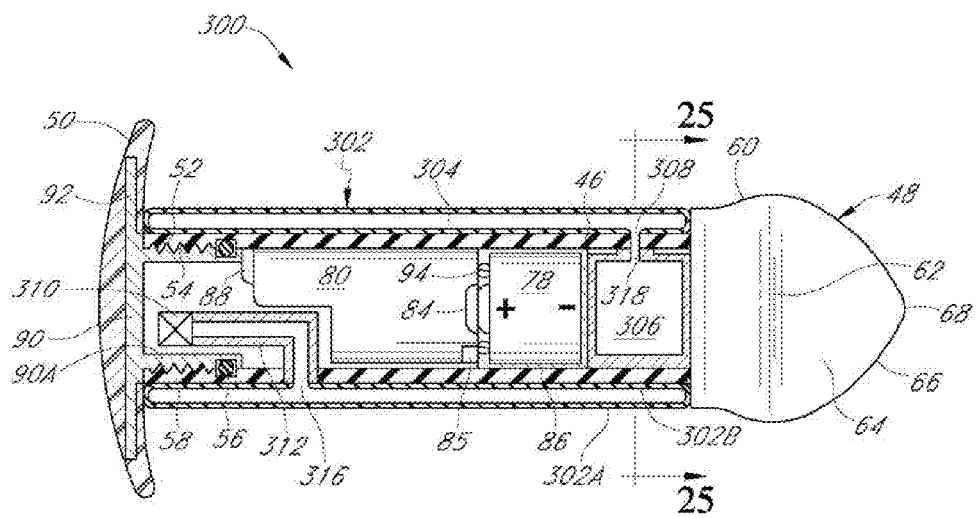
FIG. 24
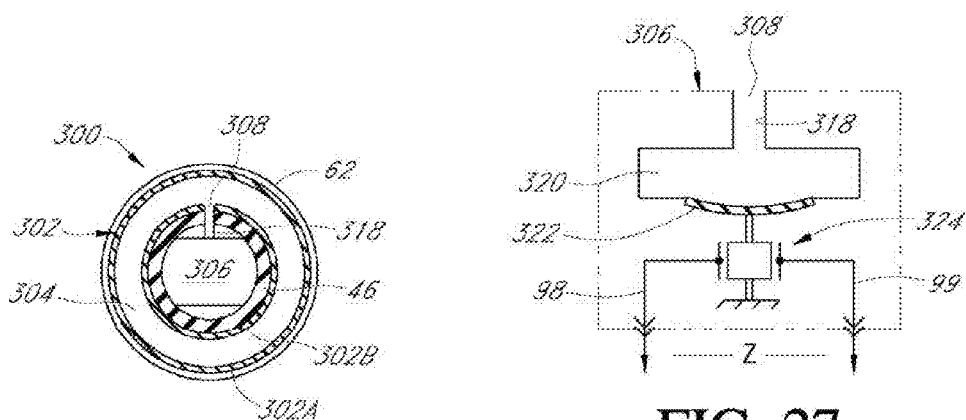
FIG. 25
FIG. 27
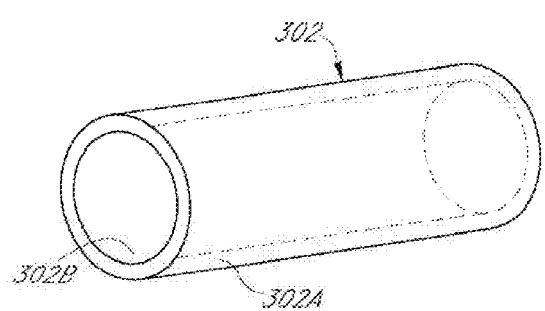
FIG. 26

MULTI-MODE PELVIC EXERCISE PROBE

PRIORITY STATEMENT & CROSS-REFERENCE TO RELATED APPLICATIONS

This application is a continuation of U.S. patent application Ser. No. 11/621,796, entitled "Multi-Mode Pelvic Exercise Probe" and filed on Jan. 10, 2007 now U.S. Pat. No. 7,628,744 in the names of Craig A. Hoffman et al.; which is continuation-in-part of U.S. patent application Ser. No. 11/268,923, entitled "Perineometer with Wireless Biofeedback," and filed on Nov. 8, 2005 now U.S. Pat. No. 7,645,220 in the names of Craig A. Hoffman et al.; both of which are hereby incorporated by reference for all purposes.

FIELD OF THE INVENTION

This invention is related to exercise devices for rehabilitating and strengthening the muscles of the pelvic floor, particularly the collective group of muscles referred to as the female pubococcygeal and related perineal musculature.

DESCRIPTION OF THE RELATED ART

Disorders that involve the pelvic area (bladder, pelvic floor muscle, rectum and uterus) are of great concern to women and health care providers as well. The pubococcygeal muscle or pelvic floor muscle is responsible for holding all the pelvic organs within the pelvic cavity. The pelvic floor muscle consists of a deep muscle layer and a superficial muscle layer that work together to keep the pelvic organs healthy and in good working order. The muscle is suspended like a hammock at the base of the pelvis and wraps around the vagina and rectum generally in an over-under figure "8" pattern.

The lower pelvic muscles may become damaged or weakened through childbirth, lack of use, aging, or as the collateral result of surgical procedures. One of the symptoms related to a weakening of these muscles is urinary incontinence. Other pelvic disorders include chronic pelvic pain and vulvodynia (pelvic muscle dysfunction) that are sometimes experienced by young adult women. These disorders are caused by involuntary contractions (spasms) of the levator ani and perineal muscles. This condition, sometimes referred to as vaginismus or pelvic floor tension myalgia, is accompanied by difficult and painful penetration of the vagina.

Various exercise devices have been developed in an attempt to restore the pelvic floor muscles, with the specific goal of strengthening the muscles that surround the urethra to overcome urinary incontinence in women. The field of pelvic muscle rehabilitation in the treatment of urinary incontinence has its origins in the pioneering work of Dr. Arnold H. Kegel and his perineometer invention disclosed in U.S. Pat. No. 2,507,858, issued to Dr. Kegel in 1950.

Dr. Kegel's perineometer was the first instrument to use biofeedback to objectively assess pelvic muscle strength, both in the physician's office, and in daily at-home use by the patient. His perineometer consisted of an inflatable vaginal probe connected by an air tube to an air pressure gauge whose dial was calibrated in millimeters of mercury. The device enabled a woman (and her physician) to observe the strength and duration of her pelvic muscle contractions in order to learn effective exercise technique.

Pelvic floor exercises increase the flow of blood to this region, as well as creating strength and tone to the muscle itself, which helps with healthy tissue renewal. Like any other muscle within the body, the pelvic musculature benefits from pelvic floor exercises and toning on a regular basis. In keeping with the acknowledged therapeutic effects of this technique, improvements to perineometer devices continue to be proposed, in which the biofeedback features are enhanced. For example, U.S. Pat. No. 6,063,045 issued to Wax et al. in 2001 shows a vaginal probe that includes an internal pressure sensor that is connected to an external display device via electrical conductors for monitoring the contraction of pelvic floor muscles. Biofeedback patterns formed on the display device guide the patient through an exercise routine.

More recently, an improved perineometer probe was disclosed in U.S. Published Patent Application No. 20060036188, entitled "Perineometer with Wireless Biofeedback," published Feb. 16, 2005 by Craig A. Hoffman, Gerry M. Hoffman and Michael John England. That invention features a self-contained perineometer probe for intravaginal use that communicates a wireless biofeedback signal to a small hand-held controller and display unit. The display unit provides audible and visual biofeedback signals that allow the patient to monitor her exercise efforts as self-directed or according to a prescribed training protocol, and optionally as prompted by a pre-programmed routine contained in the display unit.

Contemporary pelvic muscle training instruments are now incorporating vibrators for applying vibratory stimulation during exercise routines. Vibratory stimulation is known to have therapeutic and beneficial effects on human body tissue. Vibration at low frequencies applied to tissue increases blood circulation due to the increase in capillary dilation. The increased blood flow increases the consumption of oxygen and nutrients by muscles and improves the regeneration process. The result is improved muscle tone, elasticity and contractile capacity.

An example of vibratory stimulation is given in U.S. Pat. No. 6,905,471 to Leivseth et al., which discloses a pelvic exercise trainer in the form of a probe having a pressure sensor, a vibrator and a microprocessor circuit connected to the sensor and vibrator. The contraction of the pelvic floor muscles is repeated at intervals, and the force applied by pelvic floor muscles at each contraction is measured and compared with the highest previously registered value, which is stored in memory. The vibrator is activated at each contraction only if the contraction force attains or exceeds the most recent registered value, and only for as long as that relationship is maintained, e.g., the sensed pelvic contraction force attains or exceeds at least 80% of the last registered value.

U.S. Pat. No. 5,782,745 to Benderev discloses a pelvic exercise trainer in the form of a probe having a vibrator assembly and mechanical means for extending and retracting the assembly for the purpose of stretching the pelvic muscles. The probe is operable in a minimum profile, rest mode configuration where it exerts only base-line pressure, and operable in an extended profile, exercise mode configuration where it is capable of exerting higher pressure. A timer controls transitions between the operating modes. The vibrator assembly is operable only when the probe is in the extended configuration (exercise mode).

Notwithstanding the progress made by conventional pelvic exercise devices, there is a continuing interest in providing an improved biofeedback probe that can apply internal vibration therapy and is effective for rehabilitating and strengthening the muscles of the pelvic floor, particularly the collective group of muscles referred to as the female pubococcygeal and related perineal musculature. There is a further need for a biofeedback probe that can apply internal vibration therapy and is effective for use by women who are experiencing painful pelvic spasms (pelvic floor tension myalgia), as an aid for training pelvic muscle relaxation techniques.

SUMMARY OF THE INVENTION

The present invention provides a medical instrument in the form of a perineometer probe for training and conditioning the pelvic floor muscles, including the collective group of muscles involved in sexual response. The medical instrument of the present invention is selectively operable in a passive, reaction mode, in which audio/visual biofeedback signals proportional to pelvic muscle contractions are generated, and in an active, vibrating mode in which vibration therapy is applied directly to internal pelvic musculature with co-generation of vibration-induced tactile biofeedback signals proportional to the strength of pelvic muscle contractions; and in a combination of both modes simultaneously. The training instrument features a self-contained perineometer probe for intravaginal use that contains the vibrator apparatus and an RF transmitter that communicates a wireless biofeedback signal to a small portable transceiver and display unit. The display unit provides an audible signal and visual display that allows a patient to monitor her efforts as self-directed or according to a prescribed training protocol, and optionally as prompted by a pre-programmed routine contained in the display unit.

The invention in particular provides a perineometer probe for intravaginal use in connection with the development, training, conditioning and rehabilitation of the female pubococcygeal and related perineal musculature. The pelvic muscle exercising device includes an internal vibrator that applies vibrations through the probe directly to the pelvic floor muscles in an active exercise mode. The frequency of the vibration is controlled as a function of the sensed pelvic contraction pressure. The patient can select operation in three modes: active vibration only, passive reaction only (with or without biofeedback signal display), and a combination of active vibration and passive reaction.

According to one aspect of the invention, a perineometer probe contains pelvic muscle contraction pressure sensing circuitry and components that provide audio/visual biofeedback signals, and an internal vibrator device, for example a motor-driven vibrator or a piezoelectric vibrator, that applies therapeutic vibrations directly to the pelvic muscle in response to the magnitude of contraction pressure applied to the body of the probe while a training exercise is taking place. The vibration probe is operated via wireless transmission in association with a hand-held monitor where biofeedback signals are communicated audibly and visually for real time observation while a training exercise is underway.

According to another aspect of the invention, a perineometer probe, operating wirelessly in association with a hand-held display unit, contains pelvic pressure sensing circuitry and a mechanical vibrator, for example a motor-driven vibrator or a piezoelectric vibrator, that produces therapeutic tactile vibrations while pelvic muscle exercise is underway. According to a pelvic muscle strengthening mode of operation, the circuitry increases the vibration frequency in proportion to an increase in the magnitude of the sensed contraction pressure. In a pelvic muscle relaxation training mode of operation, the circuitry reduces the vibration frequency of vibration in proportion to a reduction in the sensed contraction pressure.

Because the probe remains inserted during exercise and the reaction member is in intimate contact with the pelvic muscles, the probe can be sensed directly and felt by the patient as the pelvic muscles are contracted against it, thus providing a passive tactile biofeedback signal either alone or in combination with active, vibration-induced tactile biofeedback signals.

BRIEF DESCRIPTION OF THE DRAWING FIGURES

FIG. 12 is simplified block diagram of an R.F. transceiver module that is contained within the perineometer probe of FIG. 1;

FIG. 13 is a front elevation view of a portable monitor with RF transceiver that receives RF wireless signals from the perineometer probe transmitter module and provides a visual display of the pressure waveform and audible feedback signals in response to pelvic contractions, and sends RF wireless mode selection command signals to the perineometer probe;

FIG. 14 is simplified circuit block diagram of the portable monitor of FIG. 13;

FIG. 24 is a side elevational view, partly in section, of a wireless perineometer probe having an inflatable transducer sleeve according to an alternative embodiment of the present invention;

FIG. 25 is a sectional view thereof, taken along the line 25-25 of FIG. 24;

FIG. 26 is a perspective view of the inflatable transducer sleeve shown in FIG. 24;

FIG. 27 is a circuit diagram of a piezoelectric transducer contained in the transducer module of FIG. 24;

DETAILED DESCRIPTION OF THE PREFERRED EMBODIMENTS OF THE INVENTION

Figure 1:
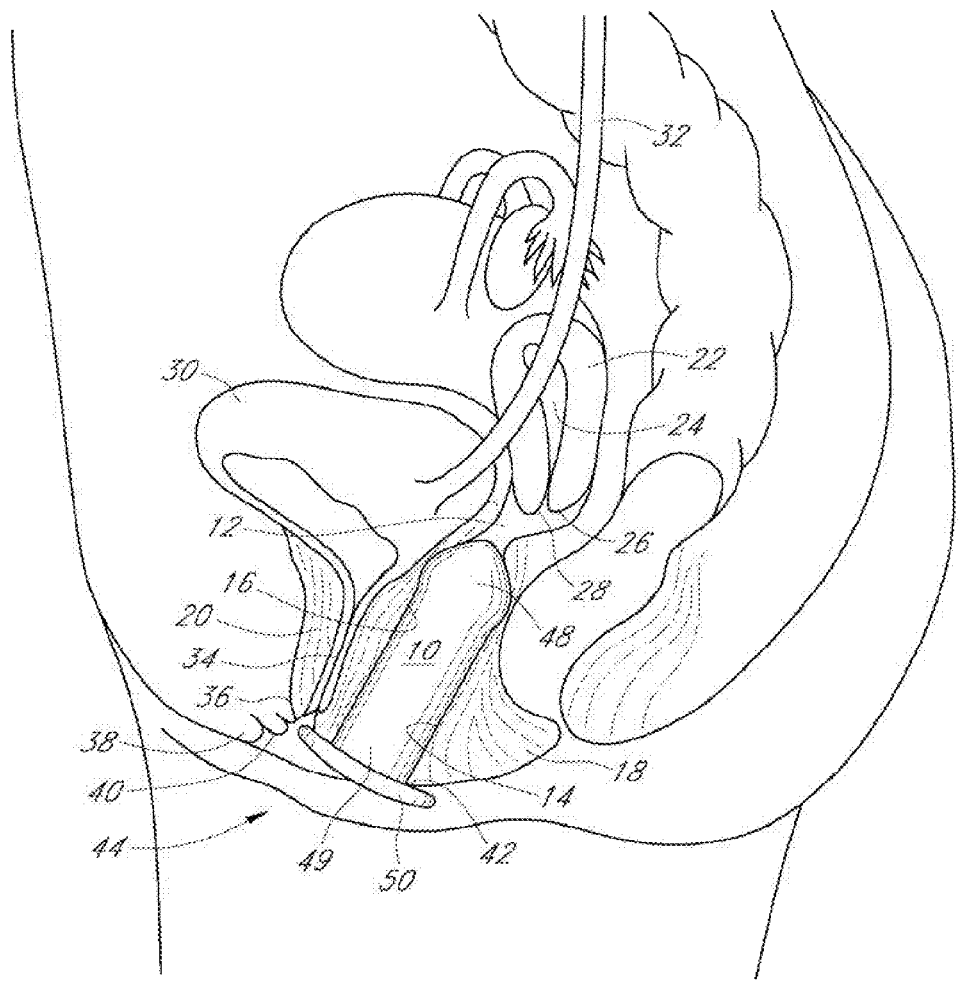
FIG. 1 is a simplified sectional view of the pelvic region of the female anatomy, showing the perineometer probe of the present invention inserted within the intravaginal cavity in the operative sensing position.
Figure 15:
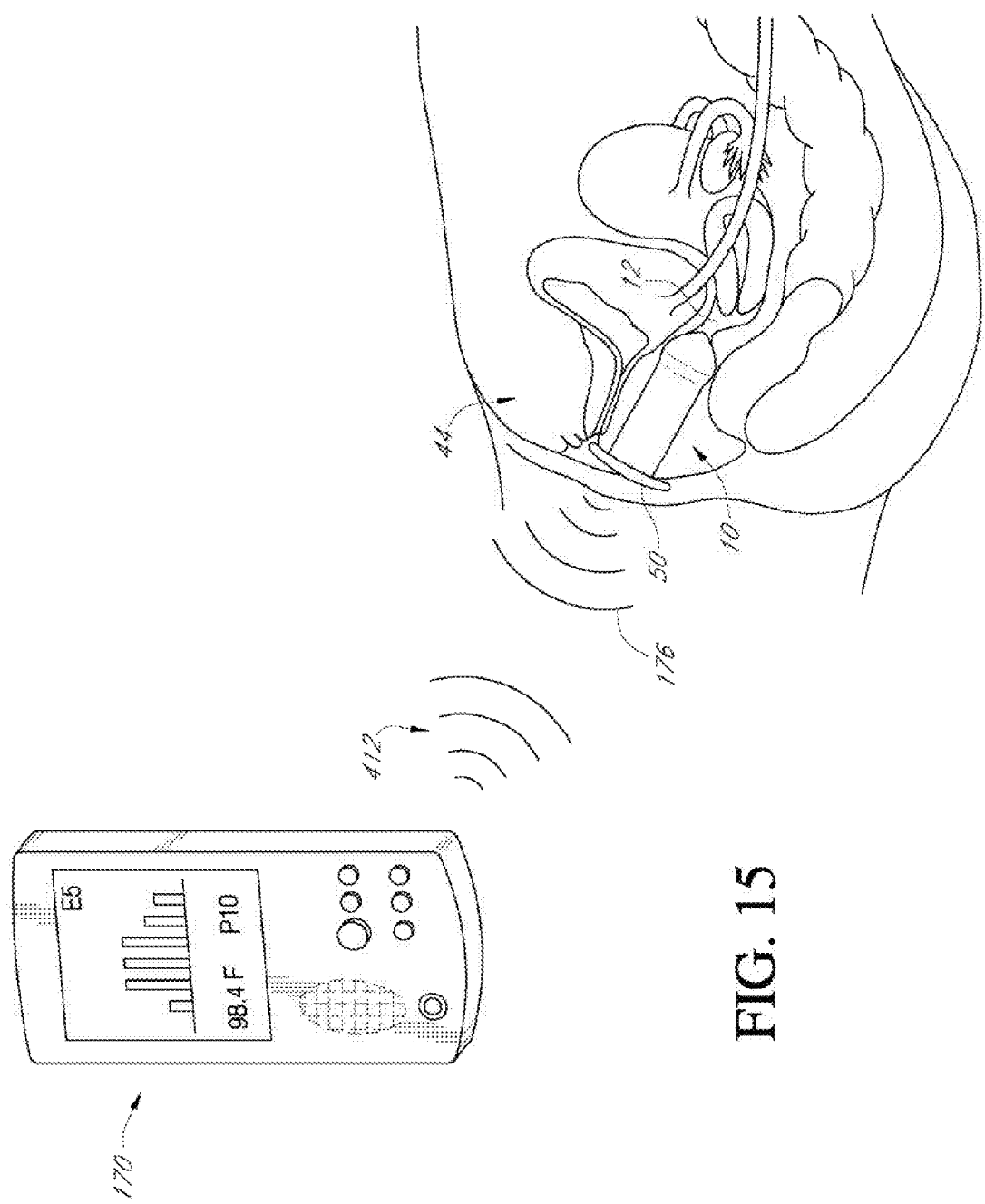
FIG. 15 is a diagram that illustrates use of the perineometer in combination with the portable monitor, by a patient in the preferred lithotomy position.

The specification that follows describes the preferred embodiments with reference to portions of the female pelvic anatomy that are shown in FIG. 1, and with reference to the lithotomy position indicted in FIG. 15. The perineometer probe 10 of the present invention is inserted in the vaginal cavity 12 while the patient is reclining in the slightly elevated lithotomy position. In that position, the patient is lying on her back, knees raised, with her head slightly elevated relative to the pelvic region. Her torso is on an approximate 30 degree angle with respect to horizontal, which results in a half-sitting position, which is the preferred position for pelvic exercise training.

Referring now to FIG. 1 and FIG. 15, the perineometer probe 10 is positioned within the vaginal cavity 12 for reacting pressure forces applied by pelvic muscle contractions. The lower wall 14 and the upper wall 16 of the vagina are connected to muscles, tissues, and nerves, that are indicated generally at 18, 20, and collectively referred to herein as the pubococcygeal and related perineal musculature. FIG. 1 also shows the uterus 22, which has an internal void known as the uterine body cavity 24, the cervix 26, the external as 28, which is the external opening of the cervix facing the vaginal cavity 12.

Other portions of the female anatomy shown in FIG. 1 include the bladder 30, ureter 32, the urethra 34, the labium minus 36, the labium majus 38, which join together in the region adjacent the clitoris 40, near the vaginal introitus 42, all clustered about the region generally known as the perineum 44.

Figure 2:
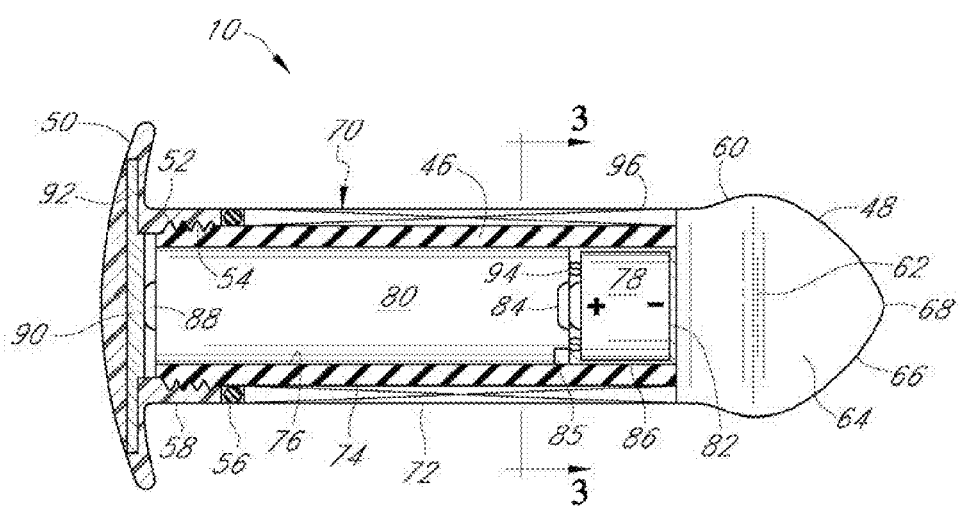
FIG. 2 is a side elevational view, partly in section, of the perineometer probe of the present invention.
Figure 4:
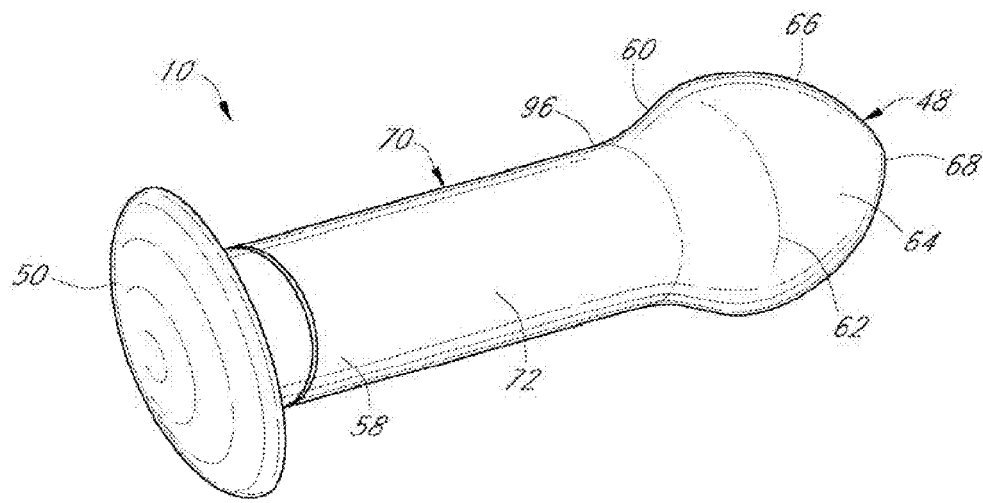
FIG. 4 is a perspective view of the perineometer probe of the present invention.

Referring now to FIG. 2 and FIG. 4, the perineometer probe 10 includes an elongated body portion or shaft 46 that is terminated on its distal end by a slightly enlarged and rounded head portion 48, and on its proximal end by a handle 50, which also functions as a closure cap. The handle 50 is fitted with threads 52 engaging mating threads 54 that are formed on the proximal end of the probe body. The interface between the handle and the probe body is sealed by an O-ring seal 56.

Figure 11:
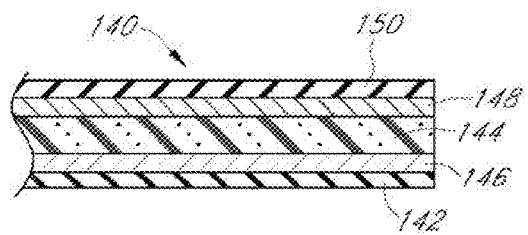
FIG. 11 is a sectional view of the flexible polymeric piezoelectric transducer sleeve, taken along the line 11-11 of FIG. 10.

As the patient is resting in the elevated lithotomy position shown in FIG. 11, the patient grasps the probe handle end 50 with her fingers. The patient then inserts the head 48 of the probe through the vaginal introitus 42 and into the vagina until the probe 10 is fully inserted, with the handle 50 engaging substantially flush against the labium minus 36. Upon full insertion, the probe head 48 extends into the vaginal cavity 12. The lower and upper vaginal walls 14, 16 close against the elongated body portion 46 to positively hold the probe 10 within the vaginal cavity.

The proximal end 58 of the elongated shaft portion 46 is adapted to seat at the introitus 42 of the vagina. The head portion 48 of the probe body is adapted to seat within the pelvic cavity 12. In the embodiment shown in FIG. 4, the head 48 is characterized by a sloping retainer surface 60 that transitions smoothly from the shaft portion 46 along an outwardly flared, conical profile until it reaches an annular rim portion 62 at the limit of the outwardly flared profile. The head portion 48 then transitions smoothly from the annular rim portion 62 along a rounded portion 64 having an inwardly sloping surface 66 that forms a tapered profile. The tapered portion is terminated on the distal end by a rounded nose portion 68, which facilitates insertion.

Figure 28:
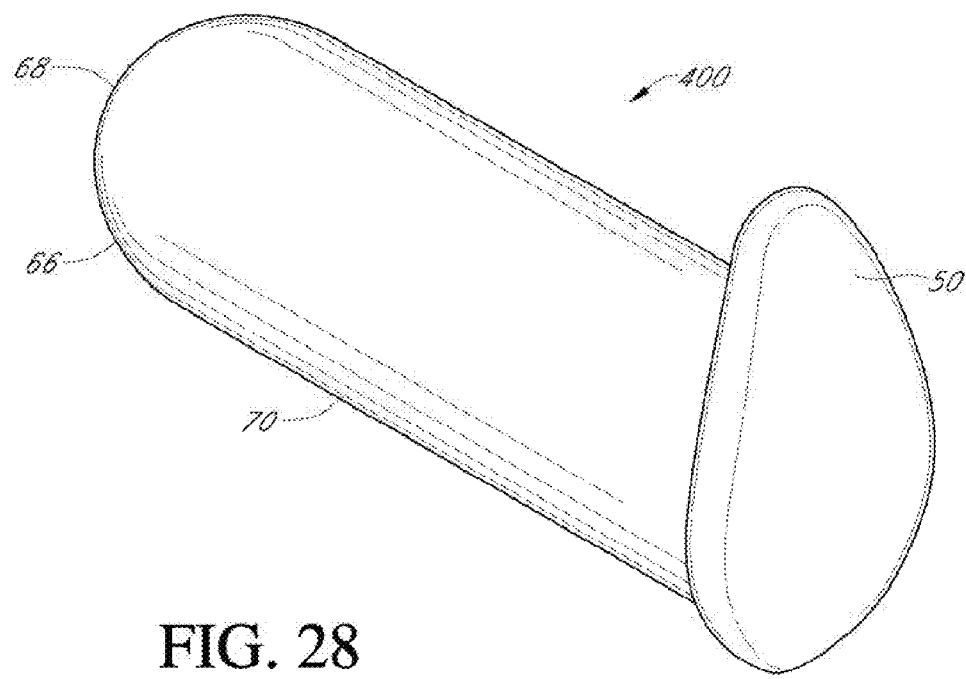
FIG. 28 is a rear perspective view of a multimode perineometer probe which incorporates an internal vibrator assembly according to an alternative embodiment of the invention.
Figure 29:
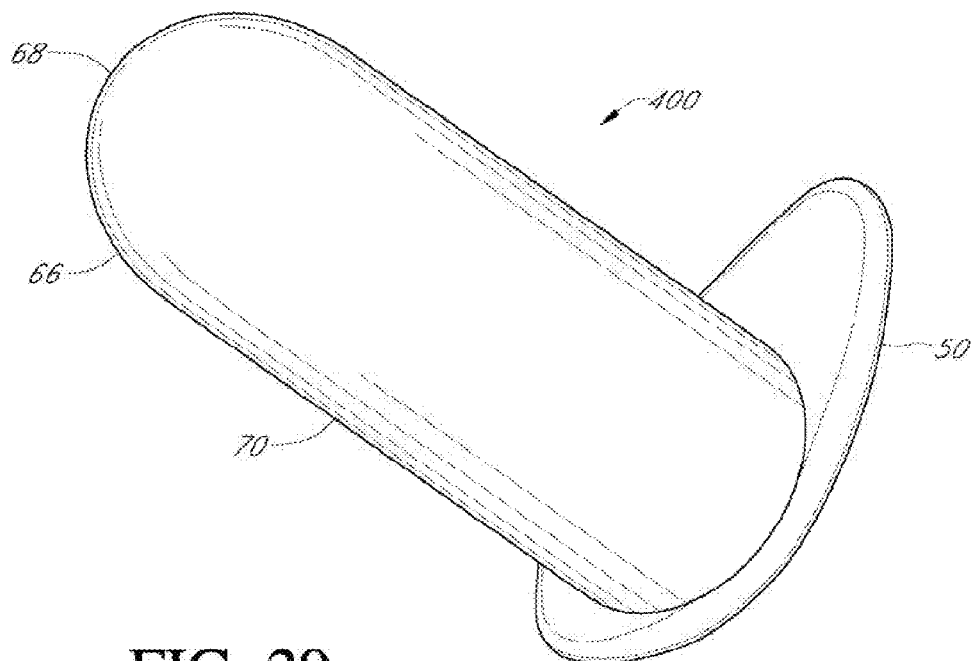
FIG. 29 is a front perspective view thereof.
Figure 30:
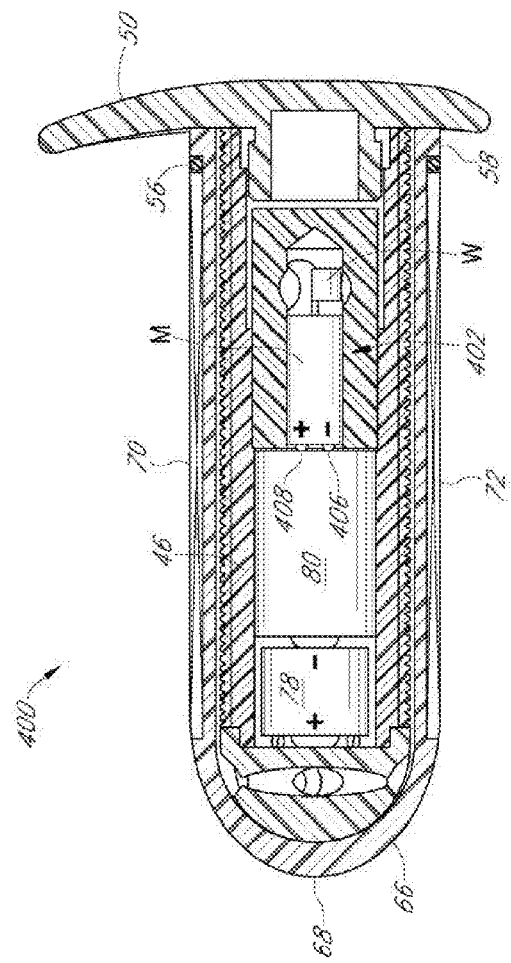
FIG. 30 is a sectional view thereof, taken along the line 30-30 of FIG. 31.
Figure 31:
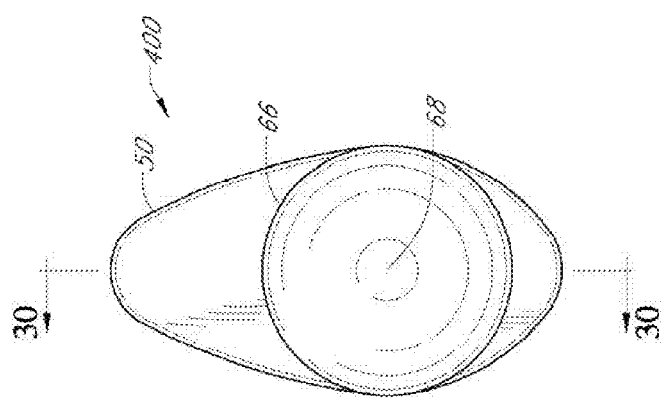
FIG. 31 is a front elevational view thereof.

Referring to the alternative embodiment shown in FIG. 28, FIG. 29 and FIG. 30, the probe 400 has a consistent diameter along it's entire shaft length.

Figure 3:
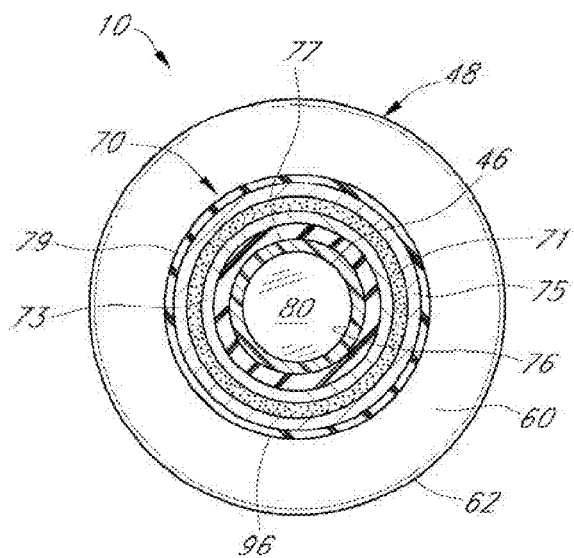
FIG. 3 is a sectional view of the perineometer probe, taken along the line 3-3 of FIG. 2.
Figure 2A:
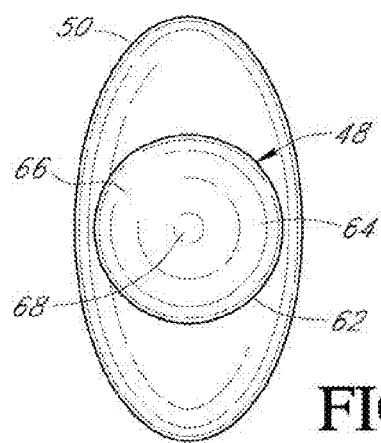
FIG. 2A is a front elevational view thereof.
Figure 5:
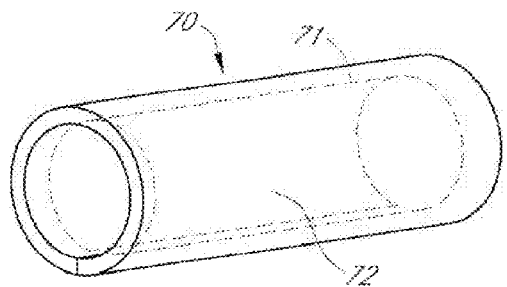
FIG. 5 is a perspective view of a transducer sleeve, shown removed from the perineometer probe.

In each probe embodiment, a pressure transducer sleeve 70 is fitted around the shaft portion 46 for sensing and providing an indication of pelvic muscle contraction pressure. As shown in FIG. 3 and FIG. 5, the transducer sleeve 70 contains a variable impedance element 71 capable of exhibiting a change in electrical impedance in response to changes in the amplitude of pressure forces applied to the transducer sleeve.

The variable impedance element 71 is distributed around and generally uniformly throughout a substantial portion of the sleeve and is sandwiched between first and second conductive electrodes 73, 75 which are disposed in electrical contact with the variable impedance element. Preferably, the conductive electrodes are formed by depositing metallization layers of a conductive metal, for example silver, on opposite side surfaces of the impedance element 71. A base layer 77 of a dielectric insulating material is applied to the external side surface of the first conductive electrode 73, and an outer layer 79 of a dielectric insulating material is applied to the external side surface of the second conductive electrode 75.

According to this probe configuration, when the pelvic floor muscles 18, 20 contract against the probe, the enlarged head portion 48 produces a differential contact zone of engagement in which the pressure forces of pelvic contraction are concentrated primarily along the externally facing contact surface 72 of the transducer sleeve 70. This clamping action creates a tight banding of pelvic muscle tissue around the transducer sleeve 10. The compressed muscle tissues 18, 20 engage against the flared retainer surface 60 of the head portion, which opposes expulsion of the probe from the vagina while a contraction is underway.

The shaft portion 46 is preferably in the form of a tubular sidewall 74 that surrounds an internal pocket 76. The distal end of the pocket 76 is sealed by the head portion 48 which forms the distal boundary of the pocket. A battery module 78, providing a supply potential E, for example, of 6 volts DC, and a signal processor circuit module 80 are received in tandem alignment within the pocket 76.

A conductive DC supply input terminal 82 is mounted in the pocket between the probe head portion 48 for electrical contact engagement against the negative terminal (−) of the battery module. The distal end of the signal processor circuit module 80 is fitted with a conductive DC supply input terminal 84 for making electrical contact against the positive terminal (+) of the battery module 78. The distal end of the signal processor circuit module 80 is also fitted with a conductive DC supply input terminal 85 for connection to the negative supply input terminal 82. A conductive interconnect portion 86, connected to the negative supply input terminal 82, extends along the tubular sidewall 74 of the shaft 46 into electrical contact engagement against the negative supply input terminal 85 of the transmitter module 80.

The proximal end of the signal processor circuit module 80 is fitted with an RF output terminal 88 for making electrical contact against an antenna input terminal portion 90 of a dipole antenna 92 that is encapsulated within the handle 50. The RF output terminal 88 engages the antenna input terminal 90 and establishes firm electrical contact when the handle 50 is tightly sealed against the probe body 46. The electrical contact terminals are also brought into electrical contact engagement with the battery electrodes and complete a series electrical circuit when the handle 50 is tightly sealed against the probe body.

According to one aspect of the invention, ON/OFF control of the DC supply voltage is provided by a bias spring 94 acting in cooperation with the handle 50. The spring 94, preferably a Belville spring washer, is interposed between the DC battery module and the signal processor circuit module 80 for urging the circuit module for movement away from electrical contact engagement with the positive terminal of the DC battery module. According with this arrangement, the handle 50 is disposed in threaded engagement with the shaft portion and engages against the circuit module 80 for moving the module axially through the pocket 76 against the bias force of the spring 94.

This spring bias action allows the DC voltage input terminal 84 of the transmitter module to be moved into and out of electrical contact engagement with the positive output terminal of the battery in response to clockwise and counter-clockwise rotation of the handle 50 relative to the shaft 46, thus making contact with the battery module and completing the DC supply circuit when the probe is activated ON, and breaking contact with the battery module and interrupting the DC supply circuit when the probe is turned OFF. The bias force of the spring 94 also maintains the RF signal output terminal 88 of the signal processor circuit module 80 in signal contact engagement with the RF signal input terminal 90 of the antenna 92 when the handle 50 is tightly sealed against the probe body.

The probe body 46, head portion 48 and handle 50 are fabricated from an injection moldable polymer material, preferably medical grade polymer resin that is a dielectric or electrically non-conductive, for example acrylic resin. The internal conductor terminals 82, 84, 86 and 90 are made of a flexible carbon impregnated conductive polymer composition which may be, for example silicone polymer. The external contact surfaces of the probe 10, including the transducer sleeve 70, are covered by a biologically inert coating layer 96 of a seamless medical grade silicone elastomer, which is preferred because of its high biocompatibility.

The silicone elastomer coating layer 96 transmits the pelvic pressure faithfully and its performance is temperature independent. Because the coating layer 96 is seamless and smooth, there are no joints or crevices to trap contaminants. Preferably, the coating layer 96 should be in the range of about $1/17$ inch-$7/16$ inch of a compressible elastomer material, which will allow shortening of the muscle fibers to induce muscle cell hypertrophy (increased muscle mass).

Figure 6:
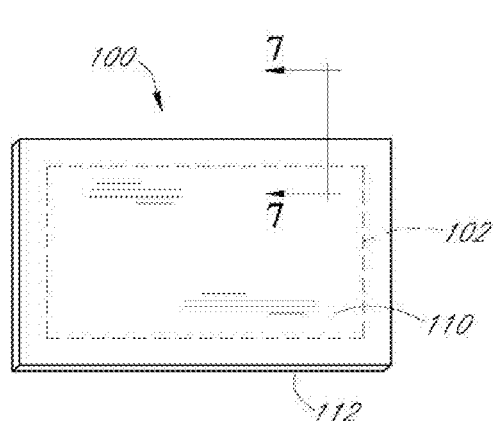
FIG. 6 is a developed plan view of a polymeric composition form transducer sleeve, shown in its flat configuration prior to assembly onto the perineometer probe.
Figure 7:
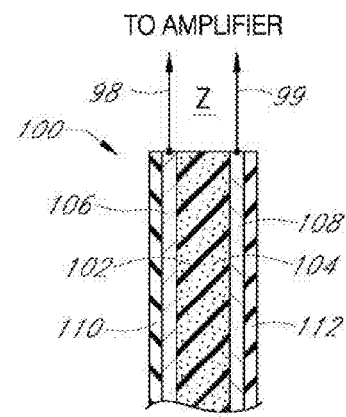
FIG. 7 is an enlarged sectional view of a portion of the polymeric composition transducer sleeve, taken along the line 7-7 of FIG. 6.

Referring now to FIG. 6 and FIG. 7, a variable impedance signal Z is conducted on signal conductors 98, 99 that are attached to the signal output nodes of a transducer 100. The impedance signal Z is proportional to pressure forces applied during contraction of the pelvic floor muscles 20, 22. This feedback signal is developed by a sensing body in which the variable impedance element is provided by commercially available transducer materials.

According to a first transducer embodiment, shown in FIG. 6 and FIG. 7, the sensing body of the transducer sleeve 100 is formed by a compressible body 102 of an insulating or weakly conductive polymer composition containing a dispersed matrix of particles 104 of at least one strongly conductive material selected from the group consisting of metals, alloys and reduced metal oxides, and first and second conductive electrodes 106, 108 disposed in electrical contact with the polymer composition. The conductive electrodes are covered by coating layers 110, 112 respectively, of a dielectric insulating polymer composition, preferably medical grade polymer resin that is a dielectric or electrically non-conductive, for example acrylic resin.

Figure 8:
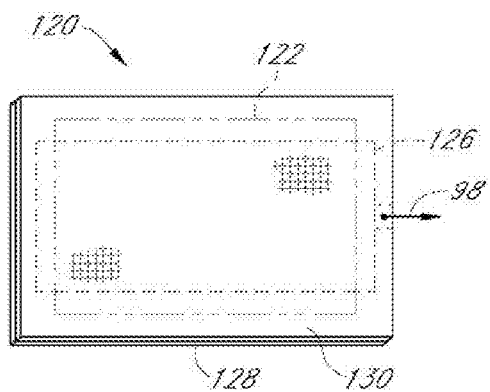
FIG. 8 is a developed plan view of a textile form fabric transducer sleeve, shown in its flat configuration prior to assembly onto the perineometer probe.
Figure 9:
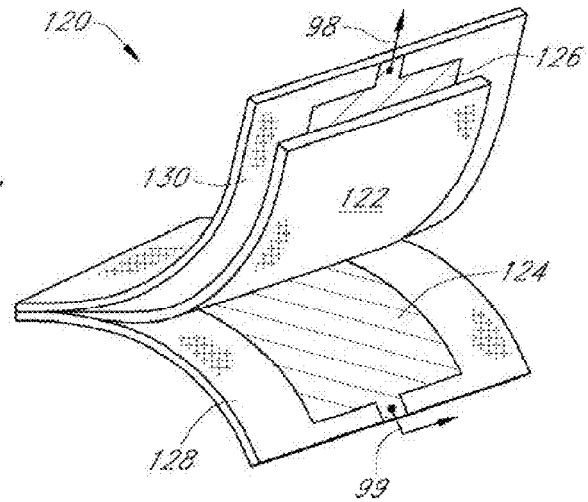
FIG. 9 is a peeled-away perspective view of the textile form fabric transducer sleeve of FIG. 8.

According to another transducer embodiment, shown in FIG. 8 and FIG. 9, the sensing body of a pressure transducer 120 is provided by a textile form variable resistance element 122 interleaved with textile form conductive members 124, 126. The variable resistance element and conductive members are enclosed between textile form non-conductive base and covering layers 128, 130. The textile layers are formed of woven nylon or polyester yarns. The conductive members are formed by printing the facing surfaces of the covering layers 128, 130 with deposits of conductive inks or polymer pastes containing metals, metal oxides or semi-conductive materials such as conductive polymers or carbon.

Preferably, the variable impedance element 122 exhibits quantum tunneling conductance when deformed. This is a well known property of polymer compositions in which a filler selected from powder-form metals or alloys, electrically conductive oxides of such elements and alloys, and admixtures thereof with a non-conductive elastomer. The filler is dispersed within the elastomer and remains structurally intact and the voids present in the starting filler powder become infilled with elastomer and particles of filler become set in close proximity during curing of the elastomer.

Figure 10:
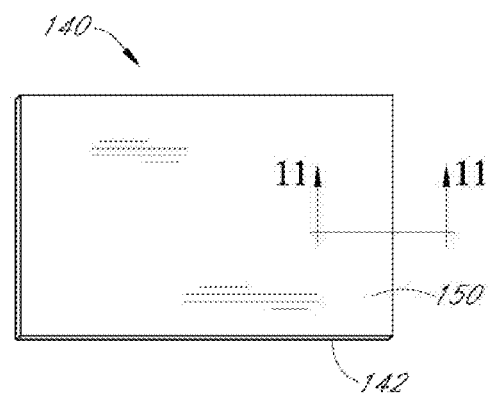
FIG. 10 is a developed plan view of a flexible polymeric piezoelectric form transducer sleeve, shown in its flat configuration prior to assembly onto the perineometer probe.

According to yet another embodiment, shown in FIG. 10 and FIG. 11, the sensing body of a pressure transducer 140 is a multi-layer flexible laminate comprising a base contact layer 142 of a flexible, non-conductive sheet material, for example, Mylar™ polyester film, a middle polymeric piezoelectric sheet 144 having moralized coating layers 146 and 148 on either side thereof, and an outer contact layer 150 of a flexible sheet material, for example, Mylar™ polyester film.

Preferably, the polymeric piezoelectric sheet 144 is a film of polyvinylidene fluoride (PVDF), a fluoroplastic resin that is commercially available as pellets for extrusion and molding. PVDF film is known to possess piezoelectric characteristics in its beta phase. Beta-phase PVDF is produced from ultra pure film by stretching it during extrusion. Both surfaces of the film extrusion are then moralized, and the film is subjected to a high voltage to polarize its atomic structure. When compressed or stretched, the polarized PVDF film generates a voltage across the moralized surfaces, in proportion to the induced strain.

The electrical equivalent or characteristic impedance Z of the piezoelectric film element 144 is a voltage source in series with a capacitance. The voltage source is the piezoelectric generator itself, and this source is directly proportional to the applied stimulus (pressure or strain). The transducer output voltage will absolutely follow the applied pressure, and the output voltage is then buffered, filtered and scaled in the signal processor module 80 before it is converted to a digital data feedback signal.

The polyester film layers 142 and 150 are adhesively attached to the metallized coating layers 146, 148 respectively. Additionally, the base layer 142 is adhesively bonded to the probe shaft 46. The piezoelectric material 144 is preferably a layer of polarized polyvinylidene fluoride (PVDF) film sandwiched between the moralized coating layers 146, 148 of electrically conductive metal. Preferably, the polymeric piezoelectric sheet 144 is approximately 28 microns in thickness, and the metallized coating layers 146, 148 are silver deposits of about 0.1 microns in thickness.

Referring again to FIGS. 4 and 5, the pressure transducer is formed by rolling a rectangular swatch of one of the transducer embodiments 100, 120 or 140 described above to produce a tubular sleeve 70 having an annular transducer body. The transducer swatch is provided in a length dimension approximately equal to the load surface length L of the probe and a width W approximately equal to the O.D. circumference of the tubular shaft sidewall 74. The transducer swatch is then rolled and adhesively bonded onto the tubular housing 64.

According to an alternative embodiment, the transducer swatch is rolled into tubular sleeve form, forming an annular body 70 as indicated in FIG. 5, and the proximal end of the probe is then inserted into the sleeve and sealed. Optionally, the transducer sleeve 70 can be molded onto the tubular sidewall 64 where a polymeric transducer material is selected.

The transducer sleeve 70 has an extended pressure-responsive area 72 that is substantially coextensive in length with the run of the pelvic floor muscles 18, 20. Consequently, when the probe 10 is fully inserted with the handle 50 engaging the labium majus 38, the pressure responsive area will span the pelvic floor muscles of most adult women.

Preferably, the transducer sleeve 70 is attached to the probe sidewall 46 by an adhesive deposit. Excellent coupling is obtained through adhesive attachment using pressure sensitive adhesive supplied by 3M Corporation, such as Product No. Y-9485. The adhesively coupled transducer sleeve 70 provides high transducer sensitivity, low mechanical and acoustic impedance to produce accurate transducer output signals throughout a broad range of loadings. The flexible transducer sleeve 70 provides a linear voltage output for a given force, enabling the sensing of movements as low as respiration and pulse. Moreover, because of the toughness and flexibility of the polymeric materials, the transducer sleeve 70 is resistant to breakage caused by rough handling.

As indicated in FIG. 12, the tubular shaft 46 serves as a reaction core member that supports the transducer sleeve 70 and reacts compression loading applied during contractions of the pelvic floor muscles 18, 20. As the pelvic floor muscles contract, the transducer sleeve 70 is stressed in accordance with changes in applied loading and yields a variable impedance output signal Z in accordance with the changes, while the support shaft 46 reacts the compression forces and provides tactile sensory feedback directly to the patient.

Referring now to FIG. 12, the variable impedance signal Z is input to the signal processor circuit module 80 via conductors 98, 99 that are electrically connected to the metallization deposit layers of the transducer. The signal processor circuit module 80 is a multiple function circuit that includes a low noise amplifier 160, an analog-to-digital converter (ADC) 162, and an RF transmitter-receiver (transceiver) 164. The analog impedance signal Z from the transducer sleeve 70 is first buffered, filtered and amplified by the low noise amplifier 160, and then converted to a digital data signal by the analog-to-digital converter (ADC) 162. Preferably, the components of the signal processor circuit module 80 are implemented by conventional RF integrated circuit (RFIC) technology.

The digitized feedback signal is input to the RF transmitter-receiver (transceiver) 164 which is operable in any frequency band which is dedicated for scientific and medical purposes. The preferred power output is 25 milliwatts (nominal) at 915 MHz (North America); 868 MHz (Europe); or other frequency bands that are set aside for industrial, scientific and medical applications, for example, 433 MHz, 2.4 GHz or 5 GHz bands. By this arrangement, the transmitted signal has an effective range of about 2 meters, which provides sufficient signal strength for reliable reception by a hand-held monitor 170.

Referring now to FIG. 13 and FIG. 14, a battery-powered, hand-held monitor 170 which includes an RF transceiver 174 that sends and receives wireless feedback signals 176 to and from the probe 10 via an internal antenna 178. The wireless feedback signals are fed into a display driver 180 that provides feedback data signals 182 to an audio and visual indicator 184. The indicator provides a graphic visual presentation of a pelvic contraction, for example the waveform 186 and audio output signals 187 in response to pelvic contractions.

The monitor 170 may also be configured to display other data, such as intravaginal temperature, for example, 98.4° F.; the elapsed time of pelvic contraction, for example E 5 (5 seconds); and the numerical pressure tension value of the contraction strength in cm water, for example P10 (10 cm water). Negative values of pelvic tension pressure (relative to the nominal "at rest" pelvic tension level) can also be displayed when the probe is used to monitor relaxation training exercises for treatment of pelvic muscle spasm disorders. Preferably, the displayed pressure tension value and the waveform are updated ten times or more per second during contractions.

The visual display presentation is implemented by a conventional liquid crystal display screen 188, preferably with backlighting. A piezoelectric speaker 190 and a headphone jack 192 provide audio output. Controls are provided for monitor power ON-OFF function (switch 194); display reset (switch 196), volume control function (dial 198); display pressure calibration (normalize pressure display to read zero for "at rest" pelvic pressure level—switch 200); pressure threshold set switch 414; and an operating mode selector switch 416. The manually selectable operating modes include: Probe Power ON—active mode (wireless signaling with vibrator power ON); Probe Power ON—passive mode (wireless signaling with vibrator power OFF); and Probe Power OFF—sleep mode (battery save).

In the above described embodiments, ultra-low power radio frequency (RF) transmission is preferred for wireless high speed data transmission to the transceiver 174. One-way or two-way wireless data communication links may be implemented. Any short range, wireless RF data communication protocol, for example, Wireless USB, Bluetooth, Wi-Fi, Zigbee, or any standard, non-standard, or proprietary wireless protocol derivative of IEEE Standard 802.14.5 may be used for this purpose.

Optionally, the probe 10 can be fitted with a thermal transducer for sensing and providing an indication of pelvic temperature, for example for monitoring the onset of ovulation. Although the probe is sealed by a removable handle in the exemplary embodiments, the probe and handle can be hermetically sealed if desired.

Alternative embodiments of the transducer sleeve are shown in FIGS. 16-23. These transducer sleeves each include one or more discrete transducer elements that are interconnected and embedded or enclosed in an annular sleeve body. In each sleeve embodiment, the impedance element of the transducer strips is constructed with a selected one of the conventional transducer materials described above.

Figure 16:
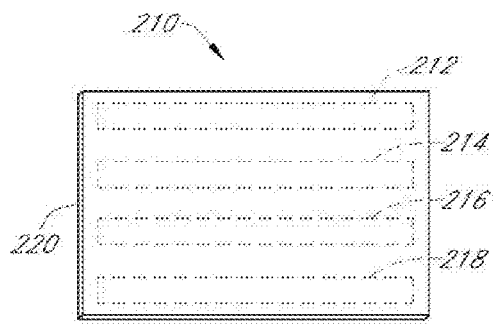
FIG. 16 is a developed plan view of a transducer sleeve with multiple strip form transducer elements, shown in its flat configuration prior to assembly onto the perineometer probe.
Figure 17:
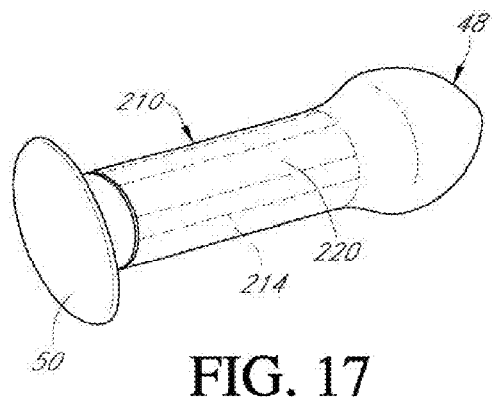
FIG. 17 is a perspective view of the strip form transducer sleeve shown assembled on a probe.

Referring to FIG. 16 and FIG. 17, a transducer sleeve 210 includes multiple discrete transducer strips 212, 214, 216 and 218 embedded or enclosed within a flexible body 220 of a compressible polymer composition, for example a closed cell polymer foam resin. The transducer strips extend along the length of the probe shaft, and are evenly spaced around the circumference of the shaft. The impedance elements are interconnected in parallel circuit relation, collectively providing a common impedance output signal Z.

Figure 18:
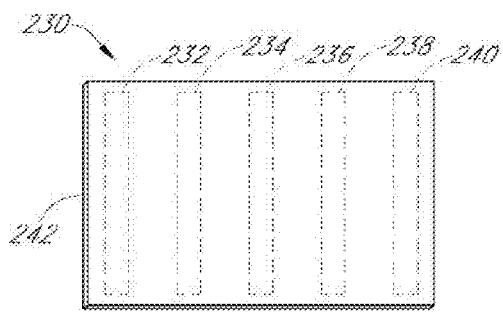
FIG. 18 is a developed plan view of a transducer sleeve with multiple band form transducer elements, shown in its flat configuration prior to assembly onto the perineometer probe.
Figure 19:
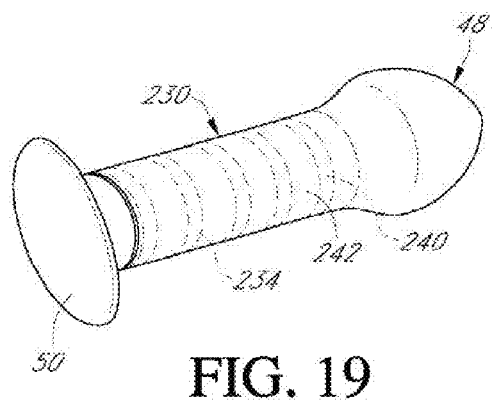
FIG. 19 is a perspective view of the multiple band form transducer sleeve shown assembled onto a probe.

Referring to FIG. 18 and FIG. 19, a transducer sleeve 230 includes multiple discrete transducer bands 232, 234, 236, 238 and 240 embedded or enclosed within a flexible body 242 of a compressible polymer composition, for example a closed cell polymer foam resin. The transducer bands encircle the probe shaft, and are evenly spaced along the length of the shaft. The impedance elements are interconnected in parallel circuit relation, providing a common impedance output signal Z.

Figure 20:
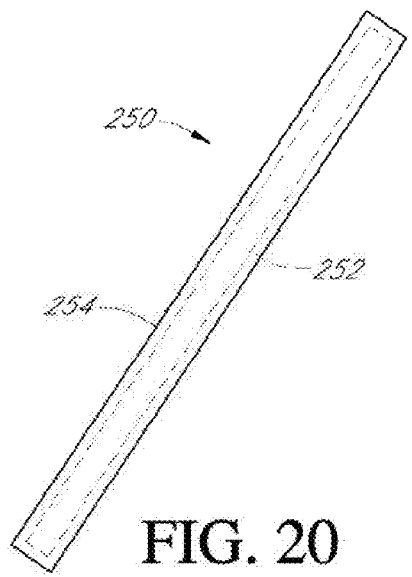
FIG. 20 is a developed plan view of a transducer sleeve with a spiral wrap transducer element, shown in its flat configuration prior to assembly onto the perineometer probe.
Figure 21:
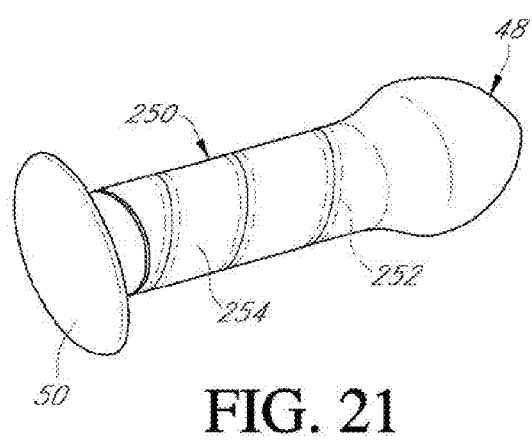
FIG. 21 is a perspective view of the spiral wrap form transducer sleeve shown assembled onto a probe.

Referring to FIG. 20 and FIG. 21, a transducer sleeve 250 includes a single elongated transducer strip 252 embedded or enclosed within a flexible body 254 of a compressible polymer composition, for example closed cell polymer foam resin. The transducer strip is wrapped around the probe shaft in a spiral pattern, and is secured thereto by an adhesive deposit. The impedance element is a continuous strip or body of a selected one of the conventional transducer materials described above.

Figure 22:
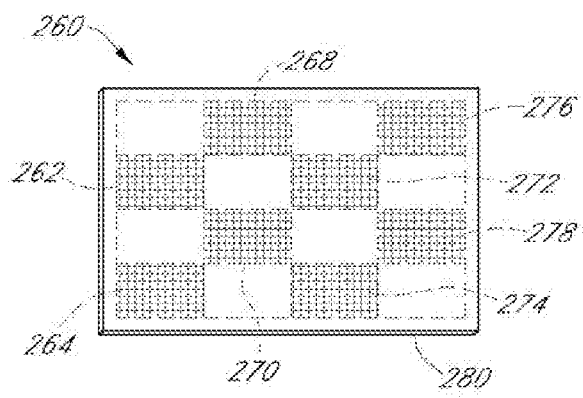
FIG. 22 is a developed plan view of a transducer sleeve with multiple transducer elements arranged in a grid pattern, shown in its flat configuration prior to assembly onto the perineometer probe.
Figure 23:
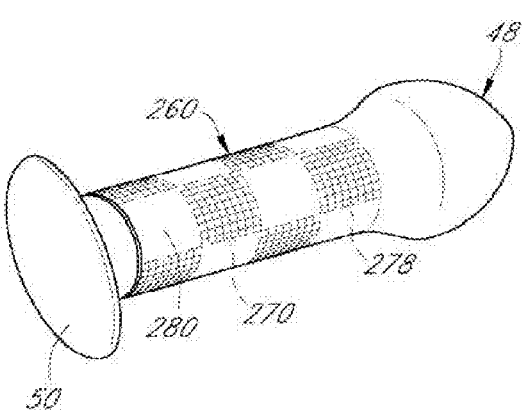
FIG. 23 is a perspective view of the grid form transducer sleeve shown assembled onto a probe.

Referring to FIG. 22 and FIG. 23, a transducer sleeve 260 includes multiple discrete transducer patches 262, 264, 266, 268 and 270 arranged in a checker board pattern and embedded or enclosed within a flexible body 272 of a compressible polymer composition, for example closed cell polymer foam resin. The transducer patches are evenly spaced apart in a rectangular grid array throughout the sleeve body. The impedance elements of the patches are interconnected in parallel circuit relation, providing a common impedance output signal Z.

An alternative wireless perineometer probe 300 is shown in FIGS. 24-27. In this embodiment, an air bladder 302 senses pelvic contraction pressure. The air bladder 302 is in the form of an elongated, annular sleeve having an outer sidewall 302A and an inner sidewall 302B separated by an annular air pressure chamber 304. The air bladder 302 is fitted around and attached to the shaft 46, preferably by an adhesive deposit, and is coupled in fluid communication with a pressure transducer module 306 via an inlet port 308 that intersects the shaft sidewall 46.

Although a double-walled bladder is illustrated, a single-wall bladder, hermetically sealed around the shaft 46 on its proximal and distal ends, can be substituted. Various medical grade rubber materials can be used to fabricate the bladder. Preferably, the bladder is fabricated of a seamless, medical grade, low-modulus, non-latex, soft nitrile composition, having a sidewall thickness in the range of 4 mils-6 mils.

The air bladder 302 is pressurized through a check valve 310 and fill tube 312 that are coupled in fluid communication with the annular bladder chamber 304 via an inlet port 316 that is formed through the shaft sidewall 46. Access to the check valve is provided by removing the handle 50, and the bladder chamber is pressurized manually by a small hand pump. The internal bladder pressure is communicated to the transducer module 306 via a flow passage 318 that is connected in fluid communication with an internal bellows chamber 320 disposed within the transducer module 306, as shown in FIG. 27.

A resilient membrane 322, attached across the bellows chamber, is mechanically coupled to a piezoelectric crystal transducer 324. As the membrane 322 deflects and extends, it applies mechanical stress across the crystal in proportion to the magnitude of the air pressure in the bellows chamber. The electrical impedance Z of the piezoelectric crystal transducer changes in proportion to the applied pressure, and this impedance signal is input to the transceiver module 80 via the signal conductors 98, 99. The piezoelectric crystal transducer 324 is preferably comprises natural, reprocessed crystalline quartz with a long discharge time constant operable in the charge mode as a dynamic pressure sensor.

The electrical equivalent or characteristic impedance Z of the piezoelectric crystal 324 is a voltage source in series with a capacitance. The voltage source is the piezoelectric generator itself, and this source is directly proportional to the applied stimulus (pressure or strain). The transducer output voltage will follow the applied pressure, and the output voltage is then buffered, filtered and scaled in the signal processor module 80 before it is converted to a digital data feedback signal. After being scaled and digitized, the pelvic contraction pressure signals are transmitted as wireless RF signals to the hand-held monitor 170, as indicated in FIG. 15.

Referring now to FIGS. 28-33, an alternative perineometer probe embodiment 400 of the present invention is selectively operable in a passive reaction mode, in which audible, visual and tactile biofeedback signals proportional to pelvic muscle contractions are generated, and in an active vibrating mode in which therapeutic vibrations are applied directly to internal pelvic musculature with or without co-generation of biofeedback signals proportional to the strength of pelvic muscle contractions; and in a combination of both modes simultaneously. The probe 400 is constructed substantially the same as the embodiment shown in FIG. 2, but with the internal components rearranged to accommodate a vibrator assembly 402.

The vibrator assembly 402 includes a DC motor M which drives a rotary eccentric weight W. The motor M is energized by a supply voltage of $V_D$ that is derived from the battery 78 via a power supply module 404. The power module 404 also supplies DC operating power to the signal processor module 80 and frequency control module 410. The vibrator supply voltage $V_D$ is applied to the motor DC input terminals 406, 408 through the variable frequency control module 410.

The output of the variable frequency control module 410 is applied to input terminals 406, 408 of the motor M. The rotary speed (rpm) of motor M is directly proportional to the amplitude of the actuating voltage output from the frequency control module 410. In the preferred embodiment, the frequency of vibration (the rotary speed or rpm of the weight W) varies in direct proportion to the amplitude of the applied voltage $V_D$, the amplitude of which is proportional to the applied pelvic contraction pressure.

The frequency control module 410 has an input terminal 412 for receiving the analog output signal 161 of the low noise amplifier 160 (FIG. 12). The output signal 161 is directly proportional to the pelvic contraction pressure sensed by the transducer 70. The frequency control module 410 scales the analog output signal 161 and outputs a vibrator driving voltage $V_D$ which varies from about zero volts DC to about 1.5 VDC. This driving voltage range corresponds to a vibration frequency range from about 1 Hz corresponding with a nominal pelvic muscle pressure exerted on the probe under relaxed, "at rest" pelvic muscle condition, to about 100 Hz corresponding to a predetermined maximum sustainable pelvic muscle pressure exerted on the probe during a deliberate, best effort pelvic contraction.

Although a linear relationship between motor RPM (vibration frequency) and contraction pressure (as represented by the vibrator driving voltage) is preferred, other functional relationships could be used as well. For example, the relationship could be non-linear, in which case the vibrator motor RPM could vary as an exponential function or as a parabolic function of the contraction pressure.

Figure 33:
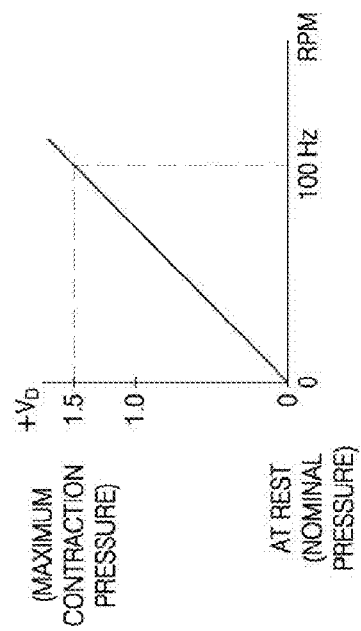
FIG. 33 is a simplified graphical plot which illustrates a proportional relationship between vibrator RPM and pelvic contraction pressure, as represented by the driving voltage $V_D$.

The output of the frequency control module 410 is normalized to zero by inserting the probe 400 into the vaginal cavity 12 as shown in FIG. 1, with the pelvic muscles 18, 20 relaxed. Then the operator manually depresses a set switch 414 that is located on the portable monitor 170 (FIG. 13). The transceiver 174 transmits a control signal to the probe that establishes a threshold voltage level which is used as a reference in the speed control module 410 for establishing zero rpm output. This corresponds to the nominal (at rest) pelvic pressure condition, as indicated in FIG. 33.

The DC motor M is preferably an ultra lightweight miniature DC motor, for example manufactured by Matsushita under Part Number V0296A, rated for a full output of 100 rpm at +1.5VDC. Optionally, a piezoelectric vibrator may be substituted.

Figure 32:
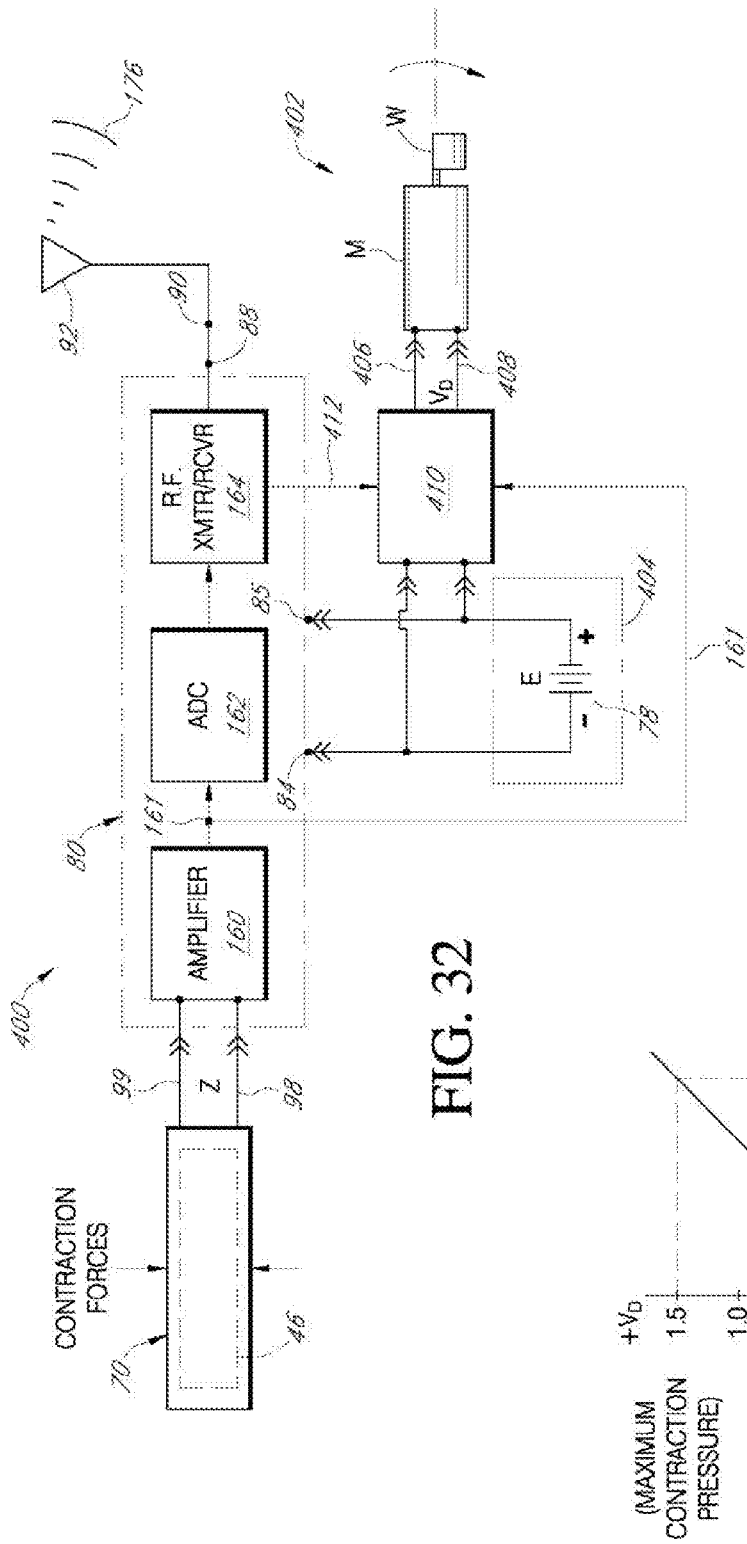
FIG. 32 is simplified circuit diagram of an R.F. transceiver and vibrator module that is contained within the multimode perineometer probe of FIG. 28.

The perineometer probe 400 is operated in cooperation with the hand-held display monitor 170, via wireless RF signaling. Referring to FIG. 13 and FIG. 32, the portable monitor 170 is equipped with a two-way transmitter-transceiver 174 for sending RF wireless mode selection command signals 412 to the perineometer probe 400. The portable monitor 170 receives RF wireless biofeedback signals 176 from the perineometer probe transmitter 164 for providing a visual display of the pelvic pressure waveform 186 and audible feedback signals 187 in response to pelvic contractions, as shown in FIG. 13 and FIG. 15.

The motor-driven vibrator assembly 402 produces therapeutic tactile vibrations while pelvic exercise is underway. According to a pelvic muscle strengthening and conditioning mode of operation, the vibration control circuitry increases the vibration frequency in proportion to an increase in the magnitude of the sensed contraction pressure. In a pelvic muscle relaxation conditioning mode of operation, the vibration control circuitry reduces the vibration frequency of vibration in proportion to a reduction in the sensed contraction pressure.

Because the probe 400 remains inserted during exercise and the sensor 70 is in intimate contact with the pelvic muscles, the body of the probe can be sensed directly and felt by the patient as the pelvic muscles are contracted against it, thus providing a passive tactile biofeedback signal either alone or in combination with active, vibration-induced tactile biofeedback signals. Multiple modes of operation can be selected manually by depressing the, ode selection switch, either (a) the passive, reaction mode, in which audio/visual biofeedback signals proportional to pelvic muscle contractions are generated, or (b) an active, vibrating mode in which vibration therapy is applied directly to internal pelvic musculature, with co-generation of vibration-induced tactile biofeedback signals proportional to the strength of pelvic muscle contractions, or (c) a combination of both modes simultaneously may be selected.

The desired operating mode is selected by the patient by depressing a membrane mode selector switch 416 on the portable monitor 170. Selection of the active, vibrating mode initiates the transmission of a wireless command signal 176 from the monitor 170 to the probe 400. The command signal is decoded in the transceiver 164, which outputs a control signal 412 (FIG. 15) that enables operation of the vibrator 402.

The perineometer encourages pelvic muscle reeducation and strengthening, by (1) giving direct tactile sensory feedback, both passive and vibration induced, to the patient during exercise which allows the patient to identify the pelvic floor muscles and confirm that the probe is properly engaged; (2) developing muscle strength and endurance due to the work required of the muscles to contract and relax against the reaction probe, thereby developing muscle memory; (3) providing audible and/or visual sensory feedback simultaneously with vibration-induced tactile sensory feedback that is directly related to performance during exercise, thus instilling patient confidence that the probe is being used properly and that the exercises are having the desired training effect; and (4) promoting strong pelvic muscle contraction and normal muscle relaxation in response to passive tactile biofeedback signals and vibration-induced tactile biofeedback signals that are communicated directly by internal contact, and by wireless biofeedback signals that are communicated in real time to the patient via a portable display monitor.

What is claimed is:

1. A probe receivable within a pelvic cavity for sensing contraction pressure applied by pelvic floor muscles against the probe, the probe comprising:
   a probe body having a head portion adapted to seat within an area of a pelvic cavity and having a shaft portion adapted to seat at the introitus of the pelvic cavity, the shaft portion ending at a distal end portion;
   a transducer sleeve fitted intermediate the distal end portion and the head portion, the transducer sleeve including a variable impedance element capable of exhibiting a change in electrical impedance in response to pelvic contraction forces applied to the transducer sleeve; and
   an electronic circuit module enclosed within the probe body and electrically coupled to the variable impedance element, the electronic circuit module including a transmitter for transmitting feedback signals in response to contraction forces applied to the transducer sleeve.

2. The probe as recited in claim 1, wherein the electronic circuit module is enclosed at least partially within the shaft portion.

3. The probe as recited in claim 1, wherein the electronic circuit module is enclosed at least partially within the distal end portion.

4. The probe as recited in claim 1, wherein the transmitter is enclosed at least partially within the distal end portion.

5. The probe as recited in claim 1, wherein the distal end portion comprises a handle.

6. The probe as recited in claim 1, wherein the distal end portion comprises a removable closure cap.

7. The probe as recited in claim 1, wherein the transducer sleeve comprises an extended pressure-responsive area that is substantially coextensive in length with shaft portion.

8. The probe as recited in claim 1, wherein the transducer sleeve comprises an adhesive deposit attached to a sidewall of the probe.

9. The probe as recited in claim 1, wherein the transducer sleeve further comprises a pressure transducer.

10. The probe as recited in claim 1, wherein the transducer sleeve further comprises transducer patches.

11. The probe as recited in claim 1, wherein the transducer sleeve is fitted in overlapping relation about a shaft portion.

12. The probe as recited in claim 1, wherein the variable impedance element is distributed around and uniformly throughout a portion of the transducer sleeve.

13. The probe as recited in claim 1, wherein the transducer sleeve and electronic circuit module cooperate to selectively operate in a passive, reaction mode in which passive tactile feedback signals are proportional to pelvic floor muscle contractions and an active, vibrating mode in which vibration therapy is applied directly, and a combination thereof.

14. The probe as recited in claim 1, wherein the transceiver transmits signals selected from the group consisting of cabled-feedback signals and wireless feedback signals transmitted by a transceiver.

15. A system for training a patient's pelvic floor muscles, comprising in combination:
   a probe body having a head portion adapted to seat within an area of a pelvic cavity and having a shaft portion adapted to seat at the introitus of the pelvic cavity, the shaft portion ending at a distal end portion;
   a transducer sleeve fitted intermediate the distal end portion and the head portion, the transducer sleeve including a variable impedance element capable of exhibiting a change in electrical impedance in response to pelvic contraction forces applied to the transducer sleeve;
   an electronic circuit module enclosed within the probe body and electrically coupled to the variable impedance element, the electronic circuit module including an RF transceiver for transmitting wireless feedback signals in response to contraction forces applied to the transducer sleeve; and
   a portable monitor including a radio frequency receiver for receiving the wireless signal and an indicator device coupled to the receiver for displaying a visual representation of feedback information contained in the wireless signal.

16. A system for exercising and training a patient's pelvic floor muscles as recited in claim 15, the indicator display device including:
   visual display apparatus for displaying an alphanumeric data representation of feedback information contained in the wireless signal.

17. A system for exercising and training a patient's pelvic floor muscles as recited in claim 15, the indicator display device including:
   visual display apparatus for displaying a visual graphic representation of feedback information contained in the wireless signal.

18. A system for exercising and training a patient's pelvic floor muscles as recited in claim 15, the indicator device including:
   audio reproduction apparatus for sounding an audible signal that corresponds to feedback information contained in the wireless signal.

19. A probe receivable within a pelvic cavity for sensing contraction pressure applied by pelvic floor muscles against the probe, the probe comprising:
   a probe body having a head portion adapted to seat within an area of a pelvic cavity and having a shaft portion adapted to seat at the introitus of the pelvic cavity, the shaft portion ending at a distal end portion;
   a transducer sleeve fitted intermediate the distal end portion and the head portion, the transducer sleeve including means for exhibiting a change in electrical impedance in response to pelvic contraction forces applied to the transducer sleeve; and
   an electronic circuit module enclosed within the probe body and electrically coupled to the variable impedance element, the electronic circuit module including a means for transmitting feedback signals in response to contraction forces applied to the transducer sleeve.

20. The probe as recited in claim 19, wherein the transducer sleeve and electronic circuit module cooperate to selectively operate in a passive, reaction mode in which passive tactile feedback signals are proportional to pelvic floor muscle contractions and an active, vibrating mode in which vibration therapy is applied directly, and a combination thereof.

* * * * *